(12) United States Patent
Vogel et al.

(10) Patent No.: US 8,916,364 B2
(45) Date of Patent: Dec. 23, 2014

(54) NITRILASES

(75) Inventors: Andreas Vogel, Leipzig (DE); Daniel Schwarze, Jena (DE); Thomas Greiner-Stoeffele, Leipzig (DE)

(73) Assignee: c-LEcta GmbH, Leipzig (DE)

( * ) Notice: Subject to any disclaimer, the term of this patent is extended or adjusted under 35 U.S.C. 154(b) by 0 days.

(21) Appl. No.: 13/878,979

(22) PCT Filed: Oct. 12, 2011

(86) PCT No.: PCT/EP2011/005115
§ 371 (c)(1),
(2), (4) Date: Jul. 5, 2013

(87) PCT Pub. No.: WO2012/048865
PCT Pub. Date: Apr. 19, 2012

(65) Prior Publication Data
US 2013/0288315 A1    Oct. 31, 2013

(30) Foreign Application Priority Data

Oct. 12, 2010   (EP) .................................... 10013548

(51) Int. Cl.
*C07K 14/195*   (2006.01)
*C12N 9/78*     (2006.01)

(52) U.S. Cl.
CPC ................ *C12N 9/78* (2013.01); *C07K 14/195* (2013.01); *C12Y 305/05001* (2013.01)
USPC ............ 435/128; 435/136; 435/146; 435/227

(58) Field of Classification Search
None
See application file for complete search history.

(56) References Cited

U.S. PATENT DOCUMENTS

| | | | |
|---|---|---|---|
| 6,870,038 | B2 | 3/2005 | Chauhan et al. |
| 7,148,051 | B2 | 12/2006 | Payne et al. |
| 7,198,927 | B2 | 4/2007 | DiCosimo et al. |
| 7,867,748 | B2 * | 1/2011 | DiCosimo et al. ............ 435/227 |
| 2006/0035352 | A1 * | 2/2006 | Payne et al. .................... 435/136 |
| 2009/0111158 | A1 | 4/2009 | DiCosimo et al. |
| 2009/0111162 | A1 | 4/2009 | DiCosimo et al. |
| 2009/0325250 | A1 | 12/2009 | DiCosimo et al. |
| 2010/0240109 | A1 | 9/2010 | DiCosimo et al. |

FOREIGN PATENT DOCUMENTS

| EP | 1 767 624 A1 | 3/2007 |
|---|---|---|
| WO | WO 2006/069110 A2 | 6/2006 |
| WO | WO 2006/069114 A2 | 6/2006 |

OTHER PUBLICATIONS

Kobayashi et al. "Primary Structure of analiphatic Nitrile-Degrading enzyme, aliphatic nitrilase from *Rhodococcus rhodochrous* K22 and expression of its gene and identification of its active site residue" 1992 Biochemistry 31 9000-9007.*

Wu et al "Protein Engineering of nitrilase fir chemoenzymatic productionof glycolic acid" 2008 Biotechnology and Bioengineering 3 717-720.*

Kobayahsi et al. "Purification and characterization of a novel nitrilase of *Phodococcus rhodochrous* K22 that acts on aliphatic nitriles" 1990 J. Bacteriol. 172 4807-4815.*

Ludmila Martinkováet al., "Biotransformations with nitrilases", Current Opinion in Chemical Biology, Apr. 2010, pp. 130-137, vol. 14, No. 2, Elsevier, XP-002619913. (Eight (8) pages).

Shijun Wu et al., "Protein Engineering of *Acidovorax facilis* 72W Nitrilase for Bioprocess Development", Biotechnology and Bioengineering, Jul. 1, 2007, pp. 689-693, vol. 97, No. 4, Wiley Periodicals, Inc., XP-55041811. (Five (5) pages).

Shijun Wu et al., "Protein Engineering of Nitrilase for Chemoenzymatic Production of Glycolic Acid", Biotechnology and Bioengineering, Feb. 15, 2008, pp. 717-720, vol. 99, No. 3, Wiley Periodicals, Inc., XP-55041810. (Four (4) pages).

S. Chauhan et al., "Purification, cloning, sequencing and over-expression in *Escherichia coli* of a regioselective aliphatic nitrilase from *Acidovorax facilis* 72W", Applied Microbiology and Biotechnology, Jan. 16, 2003, pp. 118-122, vol. 61, No. 2, Springer-Verlag, XP-002376999. (Five (5) pages).

Katherine T. Barglow et al., "Functional Proteomic and Structural Insights into Molecular Recognition in the Nitrilase Family Enzymes", Biochemistry, Dec. 23, 2008, pp. 13514-13523, vol. 47, No. 51, American Chemical Society, XP-002619954. (Ten (10) pages).

Grace Desantis et al., "Creation of a Productive, Highly Enantioselective Nitrilase through Gene Site Saturation Mutagenesis (GSSM)", Journal of the American Chemical Society, Sep. 24, 2003, pp. 11476-11477, vol. 125, No. 38, American Chemical Society, XP-002385384. (Two (2) pages).

International Search Report dated Nov. 2, 2012 including English-language translation. (Four (4) pages).

International Report on Patentability (PCT/IB/338) and (PCT/IB/373) dated Apr. 25, 2013. (Two (2) pages).

English-language Written Opinion (PCT/ISA/237) dated Nov. 2, 2012. (Twelve (12) pages).

* cited by examiner

*Primary Examiner* — Suzanne M Noakes
*Assistant Examiner* — Gerard Lacourciere
(74) *Attorney, Agent, or Firm* — Crowell & Moring LLP

(57) ABSTRACT

The invention relates to a nitrilase having improved activity in the reaction of a nitrile to form the corresponding carboxylic acid, in particular with respect to reacting 2-methylglutaronitrile, 1-(cyanomethyl)cyclohexane-1-carbonitrile, and benzonitrile. The nitrilase according to the invention is related to nitrilase from *acidovorax facilis*.

16 Claims, No Drawings

SEQUENCE LISTING

<160> NUMBER OF SEQ ID NOS: 8

<210> SEQ ID NO 1
<211> LENGTH: 1110
<212> TYPE: DNA
<213> ORGANISM: Acidovorax facilis

<400> SEQUENCE: 1

```
atggtgtctt acaactctaa atttctggcg gcgactgtgc aggcggagcc agtttggctc    60
gacgcggatg ctacgatcga caaatctatc ggtatcatcg aagaagcggc cagaaaggt   120
gcgtctctga tcgctttccc ggaagtattt atccctggtt acccatactg ggcgtggctc   180
ggcgacgtaa aatacagcct gagcttcact tctcgctacc acgaaaactc tctcgagctg   240
ggtgatgacc gtatgcgtcg tctccaactc gctgcacgtc gcaacaaaat tgcgctggtt   300
atgggctaca gcgagcgtga agcgggtagc cgctacctgt cccaggtttt catcgacgag   360
cgcggtgaaa ttgtcgcgaa ccgtcgtaaa ctcaagccga cccatgttga gcgcaccatc   420
tacggtgaag gtaacggcac ggatttcctc acccatgact cgcgttcgg tcgtgttggt   480
ggcctcaact gctgggagca ctttcagccg ctctccaaat tcatgatgta ctctctgggc   540
gaacaagttc atgtcgcatc ctggcctgca atgtccccgc tgcaaccgga tgttttccag   600
ctgtctatcg aagcgaatgc gaccgtcacc cgtagctatg ccatcgaggg tcagaccttc   660
gtgctgtgct ctacgcaggt tatcggtccg tctgcaatcg agacgttctg cctgaatgac   720
gaacagcgtg cgctgctgcc gcagggttgt ggttgggcgc gtatctatgg cccggatggt   780
tccgaactgg caaaacctct cgcagaagat gcggagggta tcctgtatgc ggaaatcgac   840
ctggaacaga ttcctctcgc aaaagcaggc gctgacccgg ttggccacta ttctcgtcca   900
gatgttctca gcgttcagtt cgacccacgt aaccataccc cggttcatcg tatcggcatt   960
gatggccgcc tggatgtaaa cacccgttcc cgtgtagaaa actttcgcct ccgccaggct  1020
gctgagcagg agcgtcaggc gtccaaacgc ctgggcacca agctctttga acagtctctg  1080
ctcgccgaag agccggtgcc ggctaaatga                                    1110
```

<210> SEQ ID NO 2
<211> LENGTH: 369
<212> TYPE: PRT
<213> ORGANISM: Acidovorax facilis

<400> SEQUENCE: 2

```
Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Val Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175
```

-continued

```
Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Arg Gln Ala Ser Lys Arg Leu Gly
            340                 345                 350

Thr Lys Leu Phe Glu Gln Ser Leu Ala Glu Pro Val Pro Ala
        355                 360                 365

Lys

<210> SEQ ID NO 3
<211> LENGTH: 369
<212> TYPE: PRT
<213> ORGANISM: Unknown
<220> FEATURE:
<223> OTHER INFORMATION: chemically synthesized

<400> SEQUENCE: 3

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
        35                  40                  45

Val Phe Ile Pro Gly Tyr Pro Tyr Trp Ala Trp Leu Gly Asp Pro Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160
```

```
Gly Leu Asn Cys Trp Glu His Phe Gln Pro Leu Ser Lys Phe Met Met
            165                 170                 175

Tyr Ser Leu Gly Glu Gln Val His Val Ala Ser Trp Pro Ala Met Ser
        180                 185                 190

Pro Leu Gln Pro Asp Val Phe Gln Leu Ser Ile Glu Ala Asn Ala Thr
            195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
            290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Glu Pro Val Pro Ala
            355                 360                 365

Lys

<210> SEQ ID NO 4
<211> LENGTH: 369
<212> TYPE: PRT
<213> ORGANISM: Unknown
<220> FEATURE:
<223> OTHER INFORMATION: chemically synthesized

<400> SEQUENCE: 4

Met Val Ser Tyr Asn Ser Lys Phe Leu Ala Ala Thr Val Gln Ala Glu
1               5                   10                  15

Pro Val Trp Leu Asp Ala Asp Thr Ile Asp Lys Ser Ile Gly Ile
            20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Val Lys
50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Asn Lys
                85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
            115                 120                 125

Arg Lys Leu Lys Pro Thr His Val Glu Arg Thr Ile Tyr Gly Glu Gly
        130                 135                 140
```

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
            165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
            195                 200                 205

Val Thr Arg Ser Tyr Ala Ile Glu Gly Gln Thr Phe Val Leu Cys Ser
210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Gly Trp Ala Arg Ile Tyr
            245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
            275                 280                 285

Ala Gly Ala Asp Pro Val Gly His Tyr Ser Arg Pro Asp Val Leu Ser
290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
            325                 330                 335

Leu Arg Gln Ala Ala Glu Gln Leu Arg Gln Ala Ser Lys Arg Leu Gly
            340                 345                 350

Thr Lys Leu Phe Glu Gln Ser Leu Leu Ala Glu Glu Pro Val Pro Ala
            355                 360                 365

Lys

<210> SEQ ID NO 5
<211> LENGTH: 369
<212> TYPE: PRT
<213> ORGANISM: Unknown
<220> FEATURE:
<223> OTHER INFORMATION: chemically synthesized

<400> SEQUENCE: 5

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Pro Lys
50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
            85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Glu Ile Val Ala Asn Arg
            115                 120                 125

```
Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
                180                 185                 190

Pro Leu Gln Pro Asp Val Phe Gln Leu Ser Ile Glu Asn Ala Thr
                195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
                260                 265                 270

Gly Ile Leu Tyr Ala Glu Ile Asp Leu Glu Gln Ile Leu Leu Ala Lys
                275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
                340                 345                 350

Thr Lys Leu Phe Glu Gln Ser Leu Leu Ala Glu Pro Val Pro Ala
                355                 360                 365

Lys

<210> SEQ ID NO 6
<211> LENGTH: 369
<212> TYPE: PRT
<213> ORGANISM: Unknown
<220> FEATURE:
<223> OTHER INFORMATION: chemically synthesized

<400> SEQUENCE: 6

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
                20                  25                  30

Ile Glu Glu Ala Ala Gln Lys Gly Ala Ser Leu Ile Ala Phe Pro Glu
            35                  40                  45

Val Phe Ile Pro Gly Tyr Pro Tyr Trp Ala Trp Leu Gly Asp Pro Lys
    50                  55                  60

Tyr Ser Leu Ser Phe Thr Ser Arg Tyr His Glu Asn Ser Leu Glu Leu
65                  70                  75                  80

Gly Asp Asp Arg Met Arg Arg Leu Gln Leu Ala Ala Arg Arg Asn Lys
                85                  90                  95

Ile Ala Leu Val Met Gly Tyr Ser Glu Arg Glu Ala Gly Ser Arg Tyr
            100                 105                 110
```

```
Leu Ser Gln Val Phe Ile Asp Glu Arg Gly Glu Ile Val Ala Asn Arg
        115                 120                 125

Arg Lys Leu Lys Pro Thr His Val Glu Arg Thr Ile Tyr Gly Glu Gly
    130                 135                 140

Asn Gly Thr Asp Phe Leu Thr His Asp Phe Ala Phe Gly Arg Val Gly
145                 150                 155                 160

Gly Leu Asn Cys Trp Glu His Val Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Pro Val Pro Ala
        355                 360                 365

Lys

<210> SEQ ID NO 7
<211> LENGTH: 381
<212> TYPE: PRT
<213> ORGANISM: Unknown
<220> FEATURE:
<223> OTHER INFORMATION: chemically synthesized

<400> SEQUENCE: 7

Met Leu Thr Tyr Lys Gly Val Phe Lys Ala Ala Thr Val Gln Ala Glu
1               5                   10                  15

Pro Val Trp Met Asp Ala Asp Ala Thr Ile Thr Lys Ala Ile Arg Ile
                20                  25                  30

Ile Glu Glu Ala Ala Asp Asn Gly Ala Lys Phe Val Ala Phe Pro Glu
            35                  40                  45

Val Phe Ile Pro Gly Tyr Pro Trp Trp Ile Trp Leu Gly Thr Ala Met
        50                  55                  60

Trp Gly Ala Lys Phe Val Val Pro Phe His Glu Asn Cys Leu Glu Leu
65                  70                  75                  80

Gly Asp Lys Arg Met Gln Arg Ile Gln Ala Ala Lys Gln Asn Gly
                85                  90                  95
```

```
Ile Ala Leu Val Met Gly Tyr Gly Glu Arg Asp Gly Ser Arg Tyr
            100                 105                 110

Met Ser Gln Val Phe Ile Asp Asp Ser Gly Lys Ile Val Ala Asn Arg
        115                 120                 125

Arg Lys Leu Lys Pro Thr His Glu Glu Arg Thr Ile Phe Gly Glu Gly
        130                 135                 140

Asn Gly Ser Asp Phe Ile Thr His Asp Phe Pro Phe Ala Arg Val Gly
145                 150                 155                 160

Gly Phe Asn Cys Trp Glu His Leu Gln Pro Leu Ser Lys Tyr Met Met
                165                 170                 175

Tyr Ser Leu Gln Glu Gln Val His Val Ala Ser Trp Pro Ala Met Cys
            180                 185                 190

Thr Tyr Gln Pro Asp Val Pro Gln Leu Gly Ala Gly Ala Asn Glu Ala
        195                 200                 205

Val Thr Arg Ser Tyr Ala Ile Glu Gly Ala Cys Tyr Val Leu Gly Ala
        210                 215                 220

Thr Leu Val Ile Gly Lys Ala Ala His Asp Ala Phe Cys Asp Thr Glu
225                 230                 235                 240

Glu His His Lys Leu Leu Gly Met Gly Gly Trp Ala Arg Ile Phe
                245                 250                 255

Gly Pro Asp Gly Glu Tyr Leu Ala Glu Ser Leu Ala His Asp Ala Glu
            260                 265                 270

Gly Ile Leu Tyr Ala Asp Ile Asp Leu Ser Lys Ile Leu Ala Lys
                275                 280                 285

Ala Asn Thr Asp Thr Val Gly His Tyr Ala Arg Pro Asp Val Leu Ser
        290                 295                 300

Leu Leu Val Asn Thr His Asn Pro Gly Pro Val Arg Tyr Leu Asp Glu
305                 310                 315                 320

Glu Gly Arg Gln Val Ser Thr Ser Ile Arg Arg His Glu Lys Leu Glu
            325                 330                 335

Gly Gln Ser Leu Asp Leu Glu Val Thr Pro Ala Thr Pro Ala Thr Leu
        340                 345                 350

Asp Ile Ala Ser Leu Val Gln Gln Ala Lys Pro Ser Thr Val Lys Ser
        355                 360                 365

Glu Ser Asn Ala Ser Thr Lys Gln Pro Asp Leu Ala Val
        370                 375                 380

<210> SEQ ID NO 8
<211> LENGTH: 369
<212> TYPE: PRT
<213> ORGANISM: Unknown
<220> FEATURE:
<223> OTHER INFORMATION: chemically synthesized

<400> SEQUENCE: 8

Met Leu Thr Tyr Lys Gly Val Phe Lys Ala Ala Thr Val Gln Ala Glu
1               5                   10                  15

Pro Val Trp Met Asp Ala Asp Ala Thr Ile Thr Lys Ala Ile Arg Ile
            20                  25                  30

Ile Glu Glu Ala Ala Asp Asn Gly Ala Lys Phe Val Ala Phe Pro Glu
        35                  40                  45

Val Phe Ile Pro Gly Tyr Pro Tyr Trp Ala Trp Leu Gly Asp Pro Lys
    50                  55                  60

Tyr Ser Leu Ser Phe Thr Ser Arg Tyr His Glu Asn Ser Leu Glu Leu
65                  70                  75                  80
```

-continued

```
Gly Asp Asp Arg Met Arg Arg Leu Gln Leu Ala Ala Arg Gln Asn Lys
                85                  90                  95
Ile Ala Leu Val Met Gly Tyr Ser Glu Arg Glu Ala Gly Ser Arg Tyr
            100                 105                 110
Leu Ser Gln Val Phe Ile Asp Glu Arg Gly Glu Ile Val Ala Asn Arg
            115                 120                 125
Arg Lys Leu Lys Pro Thr His Val Glu Arg Thr Ile Tyr Gly Glu Gly
    130                 135                 140
Asn Gly Thr Asp Phe Leu Thr His Asp Phe Ala Phe Gly Arg Val Gly
145                 150                 155                 160
Gly Leu Asn Cys Trp Glu His Val Gln Pro Leu Ser Lys Phe Met Met
                165                 170                 175
Tyr Ser Leu Gly Glu Gln Val His Val Ala Ser Trp Pro Ala Met Ser
            180                 185                 190
Pro Tyr Gln Pro Asp Val Phe Gln Leu Ser Ile Glu Ala Asn Ala Ala
            195                 200                 205
Val Thr Arg Ser Tyr Ala Ile Glu Gly Gln Thr Phe Val Leu Cys Ser
    210                 215                 220
Thr Gln Val Ile Gly Pro Ser Ala Ile Glu Thr Phe Cys Leu Asn Asp
225                 230                 235                 240
Glu Gln Arg Ala Leu Leu Pro Gln Gly Gly Gly Trp Ala Arg Ile Tyr
                245                 250                 255
Gly Pro Asp Gly Ser Glu Leu Ala Lys Pro Leu Ala Glu Asp Ala Glu
                260                 265                 270
Gly Ile Leu Tyr Ala Gly Ile Asp Leu Glu Gln Ile Leu Leu Ala Lys
            275                 280                 285
Ala Gly Ala Asp Pro Val Gly His Tyr Ser Arg Pro Asp Val Leu Ser
    290                 295                 300
Leu Gln Phe Asp Pro Arg Asn His Thr Pro Val His Arg Ile Gly Ile
305                 310                 315                 320
Asp Gly Arg Leu Asp Val Asn Thr Arg Ser Arg Val Glu Asn Phe Arg
                325                 330                 335
Leu Arg Gln Ala Ala Glu Gln Glu Arg Gln Ala Ser Lys Arg Leu Gly
                340                 345                 350
Thr Lys Leu Phe Glu Gln Ser Leu Leu Ala Glu Glu Pro Val Pro Ala
            355                 360                 365
Lys
```

NITRILASES

This application is a national stage of PCT International Application No. PCT/EP2011/005115, filed Oct. 12, 2011, which claims priority under 35 U.S.C. §119 to European Patent Application No. 10013548.2, filed Oct. 12, 2010, the entire disclosure of which is herein expressly incorporated by reference.

The invention relates to nitrilases having increased activity and temperature stability. Nitrilases are used for synthesizing carboxylic acids from the corresponding nitriles. They are distinguished from chemical catalysts by milder reaction conditions and are preferably used for regioselective and stereoselective hydrolyses in which there is to date no chemical alternative. The use of nitrilases for synthesizing carboxylic acids is described in the literature (R. Singh, R. Sharma, N. Tewari, and D. S. Rawat. *Chem Biodivers.* 3 (12):1279-1287, 2006).

In order to be able to achieve an inexpensive synthesis process, preferably nitrilases are used which have a high specific activity and long process stability. As a result, it is possible to use a smaller amount of catalyst. A high process stability correlates for the most part with an increased temperature stability of the enzymes. An enzyme having increased temperature stability has, moreover, the advantage that the process can be carried out effectively even at relatively high temperatures, which frequently leads to still faster reaction times.

Nitrilases have been isolated from various microorganisms, e.g. from the genera *Aspergillus, Arthrobacter, Geobacillus, Fusarium, Norcadia, Rhodococcus, Alcaligenes, Acidovorax, Acinetobacter, Bradyrhizopium, Pseudomonas, Pyrococcus, Bacillus* (R. N. Thuku, D. Brady, M. J. Benedik, and B. T. Sewell. *Journal of Applied Microbiology* 106 (3): 703-727, 2009; C. O'Reilly and P. D. Turner. *Journal of Applied Microbiology* 95 (6):1161-1174, 2003).

The nitrilase from *Acidovorax facilis* was first described in U.S. Pat. No. 6,870,038. Heterologous expression of the enzyme in *E. coli* led to an increase in the activity per biomass by around a factor of 3 (U.S. Pat. No. 6,870,038).

One possibility for improving enzymes is the application of enzyme engineering. Enzyme engineering is directed to the development of variants of a parent enzyme having improved properties.

Mutations for increasing the activity of a nitrilase for producing 3-hydroxyvaleric acid are described in: S. Wu, A. J. Fogiel, K. L. Petrillo, E. C. Hann, L. J. Mersinger, R. DiCosimo, D. P. O'Keefe, A. Ben Bassat, and M. S. Payne. *Biotechnol. Bioeng.* 97 (4):689-693, 2007 and U.S. Pat. No. 7,148,051. An exchange of the amino acids at positions T210 to give A or C, and at F168 to give K, V or L, led to an increased activity. Further mutations of *Acidovorax facilis* nitrilase are described in S. Wu, A. J. Fogiel, K. L. Petrillo, R. E. Jackson, K. N. Parker, R. DiCosimo, A. Ben Bassat, D. P. O'Keefe, and M. S. Payne. *Biotechnol. Bioeng.* 99 (3):717-720, 2008, and U.S. Pat. No. 7,198,927. There, a description is given of an increase in activity for the synthesis of glycolic acid from glycolonitrile for the single mutations F168 to V, K, M, T, L201 to N, Q, K, H, S, T, A, G, and for some variants having combinations of these single mutations. In the case of the variant F168V, in addition, an increased temperature stability of the enzyme-containing cell suspension was established compared with the cell that contains the wild type enzyme. Here, the temperature stability of the biocatalyst was tested within the intact *E. coli* cell, which generally has a favorable effect on protein stability.

US 2009/111158 discloses a method for producing enzymatic catalysts having nitrilase activity for hydrolyzing glycolonitrile to give glycolic acid.

WO 2006/069114 relates to a method for producing glycolic acid from formaldehyde and hydrocyanic acid.

US 2010/240109 discloses a method for improving the specific activity of enzymatic catalysts having nitrilase activity in the reaction of glycolonitrile to glycolic acid in an aqueous medium.

WO 2006/069110 discloses various methods for the enzymatic production of glycolic acid from glycolonitrile.

K. T. Barglow et al., Biochemistry 2008, 47, 13514-13525 discloses functional and structural studies on molecular recognition in enzymes of the family of nitrilases.

EP 1 767 624 discloses proteins having improved nitrile hydratase activity and improved heat resistance.

L. Martinkova et al., Curr Op in Chem Biol, vol. 14, No. 2, 2010, 130-137 relates to studies on biotransformation using nitrilases.

G. DeSantis et al., J Am Chem Soc 125(83), 2003, 11476-11477 discloses generating productive, highly enantioselective nitrilases using saturation mutagenesis (GSSM).

S. Chauvan et al., Appl Microbiol Biotech, vol. 61, No. 2, 2003, 118-122 relates to the purifying, cloning, sequencing and overexpression of a regioselective aliphatic nitrilase from *Acidovorax facilis* 72 W in *E. coli*.

The object of the invention is to provide a nitrilase having improved properties. The nitrilase should be distinguished in comparison with known nitrilases by an increased activity, in such a manner that the amount of enzyme used can be decreased or the reaction times shortened. In addition, the nitrilase should have an increased stability, in particular an increased temperature stability, in order to permit longer life during the reaction catalyzed thereby. The reaction can then be carried out with a lower amount of enzyme for a longer time, or with a higher reaction rate at an increased temperature.

This object is achieved by the subject matter of the patent claims.

Surprisingly, amino acid positions have been found in the protein sequence of the nitrilase of *Acidovorax facilis* (Seq ID No: 2) which, by substitution (exchange) of the amino acids at single positions and/or by a combination of a plurality of positions, exhibit an increased activity with various substrates and/or an increased temperature stability. This effect, surprisingly, is also found in the case of isolated enzymes which are situated outside intact cells. In particular, surprisingly, amino acid positions have been identified at which single mutations simultaneously lead to an improvement in activity and stability of the enzyme. Equally surprisingly, amino acid positions have been identified, the combination of which leads to a synergistic improvement in the relevant properties of the enzyme (combinability of the single mutations).

As a consequence of the increase in activity, the amount of the enzyme used can be reduced, or the reaction times can be shortened. Both have a direct beneficial effect on the costs of synthesis and are therefore of economic importance. The improved stability, especially the temperature stability of the enzyme, permits a longer life during the reaction. The reaction can therefore be carried out with a lower amount of enzyme for a longer time, or the reaction can be carried out at a higher reaction rate at increased temperature. Both measures lead to a reduction in the costs of synthesis.

In the nitrilase gene from *Acidovorax facilis*, amino acid positions have been identified which lead to an increase in activity and stability of the enzyme. This has been found for positions L9, V63, T70, R94, F168, L194, T208, C250, V305 and D308. The substitutions in this case surprisingly led not only to an increase in activity at positions L9, V63, T70, F168, T208, C250, but also to an increase in the temperature stability at positions L9, V63, T70, R94, F168, C250, V305. Surprisingly, it was found that substitutions at the individual positions can be combined, as a result of which further increase in activity and temperature stability is achieved.

DEFINITIONS

Parent Enzyme

By parent enzyme, the nitrilase from *Acidovorax facilis* according to Seq ID 2 is meant, which is encoded by the nucleotide sequence corresponding to Seq 1. The enzyme can be produced by heterologous expression. In this case a gene having a nucleotide sequence encoding the parent enzyme is incorporated into a corresponding expression vector and introduced into a host cell. Suitable host cells are, inter alia, strains of the genus *Escherichia, Bacillus, Saccharomyces, Pichia, Hansenula* and *Kluyveromyces*.

Substitution

An improvement in the enzyme properties is achieved by a modified sequence of amino acids in the polypeptide of the parent enzyme. In a substitution, an amino acid is replaced by another. In this case, also, a plurality of amino acids can be replaced either successively or simultaneously.

Activity

The activity of the nitrilase enzymes is measured by observing the reaction catalyzed thereby of the hydrolysis of nitriles to carboxylic acids. In this reaction, various nitriles, such as 2-methylglutaronitrile (2MG), 1-(cyanomethyl)cyclohexane-1-carbonitrile (CH-dinitrile) or benzonitrile are used. One enzyme unit corresponds in this case to the hydrolysis of 1 μmol of nitrile in 1 minute under defined conditions and is reported in units (U). The reaction analysis generally proceeds via GC or HPLC analysis. Standard conditions for the studies described here are: 5 mM 2MG in 100 mM potassium phosphate buffer pH 7.0 is contacted at 30° C. for 15 min with a nitrilase in a total volume of 200 μl. The reaction solution is mixed after this time with 30 μl of 1N hydrochloric acid solution, which stops the reaction. The acidified reaction solution is extracted with 230 μl of methyl tert-butyl ether (MTBE), wherein the nitrile and the resultant carboxylic acid are transferred to the organic phase. The MTBE phase is then analyzed by gas chromatography (GC) (column: ZB-5HT (Phenomenex, Germany), 1 min at 80° C., to 130° C. at 20° C./min, 1 min at 130° C. The detection is carried out using a flame-ionization detector (FID)).

Temperature Stability

The temperature stability is measured by incubating an enzyme solution in 100 mM potassium phosphate buffer pH 7.0 with 1 mM DTT for 15 min at a defined temperature. After this time the enzyme solution is incubated for 10 min on ice. The solution is centrifuged in order to separate off insoluble components and the activity of the supernatant solution is measured. The residual activity in % is obtained by dividing the activity after the temperature treatment by the activity measured without temperature treatment.

Nitrilases catalyze the hydrolysis of nitriles to carboxylic acids without an intermediate, i.e. the reaction proceeds by addition of two water molecules in completion as far as the carboxylic acid with release of ammonia, without the amide intermediate being able to be isolated. Nitrilases are also systematically called "nitrile-aminohydrolases" (E.C. 3.5.5.1).

The invention relates to a nitrilase comprising an amino acid sequence having at least 60% homology with the amino acid sequence according to (Seq ID No: 2), which, in comparison with the nitrilase according to (Seq ID No: 2),
(i) has an activity increased by at least 15% in the reaction of a nitrile to the corresponding carboxylic acid, wherein the nitrile is preferably selected from the group consisting of 2-methylglutaronitrile, 1-(cyanomethyl)cyclohexane-1-carbonitrile and benzonitrile;
and/or
(ii) certain amino acid substitutions.

Preferred amino acid substitutions are compiled in Table 1. Particularly preferred substitutions are shown in the right-hand column. The invention also relates to all possible combinations of the amino acid substitutions shown:

TABLE 1

| AA position | Wild type AA | Substitutions having increased activity and temperature stability | preferred | particularly preferred |
|---|---|---|---|---|
| 9 | Leu | Ala, Arg, Asn, Asp, Cys, Gln, Glu, Gly, His, Ile, Lys, Met, Phe, Pro, Ser, Thr, Trp, Tyr, Val | Lys, Glu, Ile, Arg | Lys |
| 63 | Val | Ala, Arg, Asn, Asp, Cys, Gln, Glu, Gly, His, Ile, Leu, Lys, Met, Phe, Pro, Ser, Thr, Trp, Tyr | Ile, Met, Pro, Thr | Pro |
| 70 | Thr | Ala, Arg, Asn, Asp, Cys, Gln, Glu, Gly, His, Ile, Leu, Lys, Met, Phe, Pro, Ser, Trp, Tyr, Val | Ala, Cys, Asp, Glu, Phe, Gly, Ile, Leu, Met, Asn, Pro, Gln, Ser, Tyr, Arg, Val | Ile |
| 94 | Arg | Ala, Asn, Asp, Cys, Gln, Glu, Gly, His, Ile, Leu, Lys, Met, Phe, Pro, Ser, Thr, Trp, Tyr, Val | Glu, Phe, Gly, Lys, Met, Asn, Pro, Gln, Ala, Gly, His, Ile, Leu, Ser, Thr, Val, Tyr | Gln |
| 194 | Leu | Ala, Arg, Asn, Asp, Cys, Gln, Glu, Gly, His, Ile, Lys, Met, Phe, Pro, Ser, Thr, Trp, Tyr, Val | Cys, Lys, Met, Tyr | Tyr |
| 208 | Thr | Ala, Arg, Asn, Asp, Cys, Gln, Glu, Gly, His, Ile, Leu, Lys, Met, Phe, Pro, Ser, Trp, Tyr, Val | Ala, Gly, Leu | Ala |
| 250 | Cys | Ala, Arg, Asn, Asp, Gln, Glu, Gly, His, Ile, Leu, Lys, Met, Phe, Pro, Ser, Thr, Trp, Tyr, Val | Ala, Phe, Gly, Lys, Met, Arg, Ser, Thr, Tyr, His | Gly |
| 305 | Val | Ala, Arg, Asn, Asp, Cys, Gln, Glu, Gly, His, Ile, Leu, Lys, Met, Phe, Pro, Ser, Thr, Trp, Tyr | Leu, Met | Leu |
| 308 | Asp | Ala, Arg, Asn, Cys, Gln, Glu, Gly, His, Ile, Leu, Lys, Met, Phe, Pro, Ser, Thr, Trp, Tyr, Val | Asn, Trp | Asn |

Particularly preferred combinations include enzymes which contain all conceivable combinations of the substitutions V63P, F168V and C250G, as are shown, for example, in the enzyme mutants according to (Seq ID No: 3), (Seq ID No: 4), (Seq ID No: 5) and (Seq ID No: 6).

Preferred embodiments of the invention thus relate to nitrilases in which, in comparison with the wild type nitrilase from *Acidovorax facilis* (Seq ID No: 2),
the residue Leu at the position which corresponds to position 9 is exchanged for a residue selected from the group consisting of Ala, Arg, Asn, Asp, Cys, Gln, Glu, Gly, His, Ile, Lys, Met, Phe, Pro, Ser, Thr, Trp, Tyr, Val; particularly preferably selected from the group consisting of Lys, Glu, Ile, Arg; in particular Lys; and/or the residue Val at the position which corresponds to position 63 is exchanged for a residue selected from the group consisting of Ala, Arg, Asn, Asp, Cys, Gln, Glu, Gly, His, Ile, Leu, Lys, Met, Phe, Pro, Ser, Thr, Trp, Tyr; particularly preferably selected from the group consisting of Pro, Ile, Met, Thr; in particular Pro; and/or the residue Thr at the position which corresponds to position 70 is exchanged for a residue selected from the group consisting of Ala, Arg, Asn, Asp, Cys, Gln, Glu, Gly, His, Ile, Leu, Lys, Met, Phe, Pro, Ser, Trp, Tyr, Val; particularly preferably selected from the group consisting of Ile, Ala, Cys, Asp, Glu, Phe, Gly, Leu, Met, Asn, Pro, Gln, Ser, Tyr, Arg, Val; in particular Ile; and/or the residue Arg at the position which corresponds to position 94 is exchanged for a residue selected from the group consisting of Ala, Asn, Asp, Cys, Gln, Glu, Gly, His, Ile, Leu, Lys, Met, Phe, Pro, Ser, Thr, Trp, Tyr, Val; particularly preferably selected from the group consisting of Gln, Glu, Phe, Gly, Lys, Met, Asn, Pro, Ala, Gly, His, Ile, Leu, Ser, Thr, Val, Tyr; in particular Gln and/or the residue Leu at the position which corresponds to position 194 is exchanged for a residue selected from the group consisting of Ala, Arg, Asn, Asp, Cys, Gln, Glu, Gly, His, Ile, Lys, Met, Phe, Pro, Ser, Thr, Trp, Tyr, Val; particularly preferably selected from the group consisting of Tyr, Cys, Lys, Met; in particular Tyr; and/or the residue Thr at the position which corresponds to position 208 is exchanged for a residue selected from the group consisting of Ala, Arg, Asn, Asp, Cys, Gln, Glu, Gly, His, Ile, Leu, Lys, Met, Phe, Pro, Ser, Trp, Tyr, Val; particularly preferably selected from the group consisting of Ala, Gly, Leu; in particular Ala; and/or the residue Cys at the position which corresponds to position 250 is exchanged for a residue selected from the group consisting of Ala, Arg, Asn, Asp, Gln, Glu, Gly, His, Ile, Leu, Lys, Met, Phe, Pro, Ser, Thr, Trp, Tyr, Val; particularly preferably selected from the group consisting of Gly, Ala, Phe, Lys, Met, Arg, Ser, Thr, Tyr, His; in particular Gly; and/or the residue Val at the position which corresponds to position 305 is exchanged for a residue selected from the group consisting of Ala, Arg, Asn, Asp, Cys, Gln, Glu, Gly, His, Ile, Leu, Lys, Met, Phe, Pro, Ser, Thr, Trp, Tyr; particularly preferably selected from the group consisting of Leu, Met; in particular Leu; and/or the residue Asp at the position which corresponds to position 308 is exchanged for a residue selected from the group consisting of Ala, Arg, Asn, Cys, Gln, Glu, Gly, His, Ile, Leu, Lys, Met, Phe, Pro, Ser, Thr, Trp, Tyr, Val; particularly preferably selected from the group consisting of Asn, Trp; in particular Asn.

If the substitution at the position which corresponds to position 9 by an amino acid residue selected from the group consisting of Lys, Glu, Ile, Arg; preferably Lys; is defined as "A"; the substitution at the position which corresponds to position 63 by an amino acid residue selected from the group consisting of Pro, Ile, Met, Thr; preferably Pro; as "B"; the substitution at the position which corresponds to position 70 by an amino acid residue selected from the group consisting of Ile, Ala, Cys, Asp, Glu, Phe, Gly, Leu, Met, Asn, Pro, Gln, Ser, Tyr, Arg, Val; preferably Ile; as "C"; the substitution at the position which corresponds to position 94 by an amino acid residue selected from the group consisting of Gln, Glu, Phe, Gly, Lys, Met, Asn, Pro, Ala, Gly, His, Ile, Leu, Ser, Thr, Val, Tyr; preferably Gln; as "D"; the substitution at the position which corresponds to position 168 by Val as "E"; the substitution at the position which corresponds to position 194 by an amino acid residue selected from the group consisting of Tyr, Cys, Lys, Met; preferably Tyr; as "F"; the substitution at the position which corresponds to position 208 by an amino acid residue selected from the group consisting of Ala, Gly, Leu; preferably Ala; as "G"; the substitution at the position which corresponds to position 250 by an amino acid residue selected from the group consisting of Gly, Ala, Phe, Lys, Met, Arg, Ser, Thr, Tyr, His; preferably Gly; as "H"; the substitution at the position which corresponds to position 305 by an amino acid residue selected from the group consisting of Leu, Met; preferably Leu; as "I"; and the substitution at the position which corresponds to position 308 by an amino acid residue selected from the group consisting of Asn, Trp; preferably Asn; as "J"; in each case compared with the wild type nitrilase from *Acidovorax facilis* (Seq ID No: 2), then preferred embodiments of the nitrilase according to the invention may be described in abbreviated notation as follows:

Single substitutions are preferably selected from the group consisting of A, B, C, D, E, F, G, H, I and J. In this case, for example the letter G, means that this is a nitrilase in which, in comparison with the wild type nitrilase from *Acidovorax facilis* (Seq ID No: 2), at the position which corresponds to position 208 Thr of the wild type has been exchanged for Ala, Gly or Leu, but otherwise all of the amino acid positions correspond to the wild type.

Double substitutions, in corresponding notation, are preferably selected from the group consisting of AB, AC, AD, AE, AF, AG, AH, AI, AJ, BC, BD, BE, BF, BG, BH, BI, BJ, CD, CE, CF, CG, CH, CI, CJ, DE, DF, DG, DH, DI, DJ, EF, EG, EH, EI, EJ, FG, FH, FI, FJ, GH, GI, GJ, HI, HJ and IJ.

Triple substitutions, in the corresponding notation, are preferably selected from the group consisting of ABC, ABD, ABE, ABF, ABG, ABH, ABI, ABJ, ACD, ACE, ACF, ACG, ACH, ACI, ACJ, ADE, ADF, ADG, ADH, ADI, ADJ, AEF, AEG, AEH, AEI, AEJ, AFG, AFH, AFI, AFJ, AGH, AGI, AGJ, AHI, AHJ, AIJ, BCD, BCE, BCF, BCG, BCH, BCI, BCJ, BDE, BDF, BDG, BDH, BDI, BDJ, BEF, BEG, BEH, BEI, BEJ, BFG, BFH, BFI, BFJ, BGH, BGI, BGJ, BHI, BHJ, BIJ, CDE, CDF, CDG, CDH, CDI, CDJ, CEF, CEG, CEH, CEI, CEJ, CFG, CFH, CFI, CFJ, CGH, CGI, CGJ, CHI, CHJ, CIJ, DEF, DEG, DEH, DEI, DEJ, DFG, DFH, DFI, DFJ, DGH, DGI, DGJ, DHI, DHJ, DIJ, EFG, EFH, EFI, EFJ, EGH, EGI, EGJ, EHI, EHJ, EIJ, FGH, FGI, FGJ, FHI, FHJ, FIJ, GHI, GHJ, GIJ, and HIJ.

In a preferred embodiment, the nitrilase according to the invention, in comparison with the wild type nitrilase from *Acidovorax facilis* (Seq ID No: 2), has at least four substitutions at the positionen which correspond to positions 9, 63, 70, 94, 168, 194, 208, 250, 305, or 308, wherein three of the substitutions are selected from the group consisting of ABC, ABD, ABE, ABF, ABG, ABH, ABI, ABJ, ACD, ACE, ACF, ACG, ACH, ACI, ACJ, ADE, ADF, ADG, ADH, ADI, ADJ, AEF, AEG, AEH, AEI, AEJ, AFG, AFH, AFI, AFJ, AGH, AGI, AGJ, AHI, AHJ, AIJ, BCD, BCE, BCF, BCG, BCH, BCI, BCJ, BDE, BDF, BDG, BDH, BDI, BDJ, BEF, BEG, BEH, BEI, BEJ, BFG, BFH, BFI, BFJ, BGH, BGI, BGJ, BHI, BHJ, BIJ, CDE, CDF, CDG, CDH, CDI, CDJ, CEF, CEG, CEH, CEI, CEJ, CFG, CFH, CFI, CFJ, CGH, CGI, CGJ, CHI, CHJ, CIJ, DEF, DEG, DEH, DEI, DEJ, DFG, DFHi, DFI, DFJ, DGH, DGI, DGJ, DHI, DHJ, DIJ, EFG, EFH, EFI, EFJ, EGH, EGI, EGJ, EHI, EHJ, EIJ, FGH, FGI, FGJ, FHI, FHJ, FIJ, GHI, GHJ, GIJ, and HIJ.

In a preferred embodiment, the nitrilase according to the invention, in comparison with the wild type nitrilase from *Acidovorax facilis* (Seq ID No: 2), has at least five substitutions at positions which correspond to positions 9, 63, 70, 94, 168, 194, 208, 250, 305, or 308, wherein three of these substitutions are selected from the group consisting of ABC, ABD, ABE, ABF, ABG, ABH, ABI, ABJ, ACD, ACE, ACF, ACG, ACH, ACI, ACJ, ADE, ADF, ADG, ADH, ADI, ADJ, AEF, AEG, AEH, AEI, AEJ, AFG, AFH, AFI, AFJ, AGH, AGI, AGJ, AHI, AHJ, AIJ, BCD, BCE, BCF, BCG, BCH, BCI, BCJ, BDE, BDF, BDG, BDH, BDI, BDJ, BEF, BEG, BEH, BEI, BEJ, BFG, BFH, BFI, BFJ, BGH, BGI, BGJ, BHI, BHJ, BIJ, CDE, CDF, CDG, CDH, CDI, CDJ, CEF, CEG, CEH, CEI, CEJ, CFG, CFH, CFI, CFJ, CGH, CGI, CGJ, CHI, CHJ, CIJ, DEF, DEG, DEH, DEI, DEJ, DFG, DFH, DFI, DFJ, DGH, DGI, DGJ, DHI, DHJ, DIJ, EFG, EFH, EFI, EFJ, EGH, EGI, EGJ, EHI, EHJ, EIJ, FGH, FGI, FGJ, FHI, FHJ, FIJ, GHI, GHJ, GIJ, and HIJ.

In a preferred embodiment, the nitralase according to the invention, in comparison with the wild type nitrilase from *Acidovorax facilis* (Seq ID No: 2), has at least six substitutions at positions which correspond to positions 9, 63, 70, 94, 168, 194, 208, 250, 305, or 308, wherein three of these substitutions are selected from the group consisting of ABC, ABD, ABE, ABF, ABG, ABH, ABI, ABJ, ACD, ACE, ACF, ACG, ACH, ACI, ACJ, ADE, ADF, ADG, ADH, ADI, ADJ, AEF, AEG, AEH, AEI, AEJ, AFG, AFH, AFI, AFJ, AGH, AGI, AGJ, AHI, AHJ, AIJ, BCD, BCE, BCF, BCG, BCH, BCI, BCJ, BDE, BDF, BDG, BDH, BDI, BDJ, BEF, BEG, BEH, BEI, BEJ, BFG, BFH, BFI, BFJ, BGH, BGI, BGJ, BHI, BHJ, BIJ, CDE, CDF, CDG, CDH, CDI, CDJ, CEF, CEG, CEH, CEI, CEJ, CFG, CFH, CFI, CFJ, CGH, CGI, CGJ, CHI, CHJ, CIJ, DEF, DEG, DEH, DEI, DEJ, DFG, DFH, DFI, DFJ, DGH, DGI, DGJ, DHI, DHJ, DIJ, EFG, EFH, EFI, EFJ, EGH, EGI, EGJ, EHI, EHJ, EIJ, FGH, FGI, FGJ, FHI, FHJ, FIJ, GHI, GHJ, GIJ, and HIJ.

In a preferred embodiment, the nitralase according to the invention, in comparison with the wild type nitrilase from *Acidovorax facilis* (Seq ID No: 2), has at least seven substitutions at positions which correspond to positions 9, 63, 70, 94, 168, 194, 208, 250, 305, or 308, wherein three of these substitutions are selected from the group consisting of ABC, ABD, ABE, ABF, ABG, ABH, ABI, ABJ, ACD, ACE, ACF, ACG, ACH, ACI, ACJ, ADE, ADF, ADG, ADH, ADI, ADJ, AEF, AEG, AEH, AEI, AEJ, AFG, AFH, AFI, AFJ, AGH, AGI, AGJ, AHI, AHJ, AIJ, BCD, BCE, BCF, BCG, BCH, BCI, BCJ, BDE, BDF, BDG, BDH, BDI, BDJ, BEF, BEG, BEH, BEI, BEJ, BFG, BFH, BFI, BFJ, BGH, BGI, BGJ, BHI, BHJ, BIJ, CDE, CDF, CDG, CDH, CDI, CDJ, CEF, CEG, CEH, CEI, CEJ, CFG, CFH, CFI, CFJ, CGH, CGI, CGJ, CHI, CHJ, CIJ, DEF, DEG, DEH, DEI, DEJ, DFG, DFH, DFI, DFJ, DGH, DGI, DGJ, DHI, DHJ, DIJ, EFG, EFH, EFI, EFJ, EGH, EGI, EGJ, EHI, EHJ, EIJ, FGH, FGI, FGJ, FHI, FHJ, FIJ, GHI, GHJ, GIJ, and HIJ.

In a particularly preferred embodiment, the nitrilase according to the invention has at least three, four, five, six, seven, eight, nine or ten substitutions in comparison with the wild type nitrilase from *Acidovorax facilis* (Seq ID No: 2), comprising the three substitutions V63P, F168V and C250G.

A further nitrilase according to the invention was obtained from an unculturable organism and is shown in (Seq ID No: 7). Via a suitable combination of the sequences from (Seq ID No: 1) with (Seq ID No: 7) and introduction of a combination of the substances shown in Table 1, an enzyme of the (Seq ID No: 8) was generated, which surprisingly has a greatly increased activity and temperature stability compared with the parent enzyme.

The nitrilase according to the invention, in comparison with the amino acid sequence of the nitrilase from *Acidovorax facilis* (Seq ID No: 2), preferably has a homology of at least 60%, or at least 65%, preferably at least 70%, or at least 75%, particularly preferably at least 80%, or at least 85%, very particularly preferably at least 90% or at least 92%, likewise preferably at least 93% or at least 94%, and also particularly preferably at least 95%, at least 96%, at least 97%, or at least 98%, and most preferably at least 99%.

In the context of the invention, the homology of a sequence is preferably calculated as identity by means of BLASTP 2.2.20+ (Stephen F. Altschul, Thomas L. Madden, Alejandro A. Schäffer, Jinghui Zhang, Zheng Zhang, Webb Miller, and David J. Lipman (1997)), "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schäffer, and Yi-Kuo Yu (2005)".

The position of the claimed substitutions is determined in the case of nitrilases homologous to the amino acid sequence of the nitrilase from *Acidovorax facilis* (Seq ID No: 2) from a sequence- or structure-based alignment. Methods and tools for such aligments are known to those skilled in the art. For instance, for sequence-based alignments, for example, ClustalW (Larkin M. A., Blackshields G., Brown N. P., Chema R., McGettigan P. A., McWilliam H., Valentin F., Wallace I. M., Wilm A., Lopez R., Thompson J. D., Gibson T. J. and Higgins D. G. (2007), Bioinformatics 23(21): 2947-2948), Multialign (F. CORPET, 1988, Nucl. Acids Res., 16 (22), 10881-10890) or Dialign (Subramanian A R, Hiran S, Steinkamp R, Meinicke P, Corel E, Morgenstern B., Nucleic Acids Res. 2010 Jul. 1; 38 Suppl:W19-22) and structure-based alignments by the Swiss-Model (Arnold K., Bordoli L., Kopp J., and Schwede T. (2006), Bioinformatics, 22, 195-201.), CPH models (Nielsen M., Lundegaard C., Lund O., Petersen T N, Nucleic Acids Research, 2010, Vol. 38) or Geno3D (Combet C, Jambon M, Deléage G & Geourjon C, Bioinformatics, 2002, 18, 213-214) are used.

The corresponding positions in the homologous sequences can therefore be correspondingly displaced by insertion or deletion of one or more amino acids. In addition, it is likewise possible that the correspondingly homologous nitrilases, at the positions assigned by the alignments, have a different amino acid than the nitrilase from *Acidovorax facilis* (Seq ID No: 2), such that, for example Leu9 from Seq ID No. 2 in the homologous nitrilase 1 corresponds to Ile11, in the homologous nitrilase 2 Val8 or, in the homologous nitrilase X, to the amino acid Y. This applies correspondingly to all other said positions.

The enzyme according to the invention corresponds preferably to a nitrilase having more than 60% homology with the amino acid sequence according to (Seq ID No: 2) which has at least 1, preferably at least 2, more preferably at least 3, particularly preferably at least 4, likewise preferably at least 5, and most preferably at least 6, amino acid substitution(s) selected from the following group:

a) one substitution in the position which corresponds to position 9 in (Seq ID No: 2)
b) one substitution in the position which corresponds to position 63 in (Seq ID No: 2)
c) one substitution in the position which corresponds to position 70 in (Seq ID No: 2)
d) one substitution in the position which corresponds to position 94 in (Seq ID No: 2)
e) one substitution in the position which corresponds to position 194 in (Seq ID No: 2)
f) one substitution in the position which corresponds to position 208 in (Seq ID No: 2)
g) one substitution in the position which corresponds to position 250 in (Seq ID No: 2)

h) one substitution in the position which corresponds to position 305 in (Seq ID No: 2)
i) one substitution in the position which corresponds to position 308 in (Seq ID No: 2)

and/or the enzyme, in comparison with the parent enzyme, has an activity in the reaction of a nitrile to a carboxylic acid increased by at least 15% and/or the enzyme after a temperature treatment in which the activity of the parent enzyme is reduced by at least 40%, has a residual activity increased by at least 10% in comparison with the parent enzyme.

Preference is given to the enzyme according to the invention which, in addition to the abovementioned substitutions, has a further at least 1, preferably at least 2, more preferably at least 3, particularly preferably at least 4, and most preferably at least 5, additional amino acid substitution(s) selected from the following group:

a) the residue Tyr at the position which corresponds to position 65 in (Seq ID No. 2) is exchanged for a residue selected from the group consisting of Ala, Arg, Asn, Asp, Cys, Gln, Glu, Gly, His, Ile, Leu, Lys, Met, Phe, Pro, Ser, Thr, Trp, Val; particularly preferably Cys;
b) the residue Phe at the position which corresponds to position 168 in (Seq ID No. 2) is exchanged for a residue selected from the group consisting of Ala, Arg, Asn, Asp, Cys, Gln, Glu, Gly, His, Ile, Leu, Lys, Met, Pro, Ser, Thr, Trp, Tyr, Val; particularly preferably Val;
c) the residue Phe at the position which corresponds to position 174 in (Seq ID No. 2) is exchanged for a residue selected from the group consisting of Ala, Arg, Asn, Asp, Cys, Gln, Glu, Gly, His, Ile, Leu, Lys, Met, Pro, Ser, Thr, Trp, Tyr, Val; particularly preferably Ile;
d) the residue Leu at the position which corresponds to position 201 in (Seq ID No. 2) is exchanged for a residue selected from the group consisting of Ala, Arg, Asn, Asp, Cys, Gln, Glu, Gly, His, Ile, Lys, Met, Phe, Pro, Ser, Thr, Trp, Tyr, Val; particularly preferably Asn;
e) the residue Thr at the position which corresponds to position 210 in (Seq ID No. 2) is exchanged for a residue selected from the group consisting of Ala, Arg, Asn, Asp, Cys, Gln, Glu, Gly, His, Ile, Leu, Lys, Met, Phe, Pro, Ser, Trp, Tyr, Val; particularly preferably Ala.

In a preferred embodiment, the nitrilase according to the invention has one of the following mutation combinations:
a) V63P, C250G (Seq ID No: 3)
b) F168V, C250G (Seq ID No: 4).

In a preferred embodiment, the nitrilase according to the invention is the nitrilase according to (Seq ID No: 8) or a homologous nitrilase which has the same mutations as its parent enzyme, such as (Seq ID No: 8) in comparison with (Seq ID No: 2). The nitrilase according to (Seq ID No: 8), in comparison with the parent enzyme, with CH-dinitrile, has an activity increased by 335%.

Preferably, the nitrilase according to the invention has a homology with (Seq ID No: 8) of greater than 90%, preferably greater than 93%, particularly preferably greater than 95%, very particularly preferably greater than 98%, and most preferably greater than 99%.

The nitrilase according to the invention has, in comparison with the parent enzyme (Seq ID No: 2), preferably an activity in the reaction of a nitrile to a carboxylic acid increased by 20%, preferably by 30%, more preferably by 40%, particularly preferably by 60%, also preferably by 80%, still more preferably by 150%, and most preferably by 200%.

In preferred embodiments A1-A5 to F1-F5, the nitrilase according to the invention, after a temperature treatment in which the activity of the parent enzyme is reduced by at least the percentages stated in the table hereinafter, has at least the residual activities stated in the Table 2 hereinafter in comparison with the parent enzyme (Seq ID No: 2):

TABLE 2

| No. | Inactivation of parent enzyme at least | Increased residual activity of the claimed nitrilase | | | | | |
|---|---|---|---|---|---|---|---|
| | | A | B | C | D | E | F |
| 1 | 20% | 10% | 20% | 30% | 50% | 100% | 200% |
| 2 | 40% | 10% | 20% | 30% | 50% | 100% | 200% |
| 3 | 60% | 10% | 20% | 30% | 50% | 100% | 200% |
| 4 | 80% | 10% | 20% | 30% | 50% | 100% | 200% |
| 5 | 90% | 10% | 20% | 30% | 50% | 100% | 200% |

In the table hereinbefore, for example embodiment C3 indicates that the nitrilase according to the invention, after a temperature treatment in which the activity of the parent enzyme is reduced by at least 60%, has a residual activity increased by at least 30%, preferably by at least 50%, still more preferably by at least 100%, and most preferably by at least 200%, compared with the parent enzyme.

A further aspect of the invention relates to a method for producing a carboxylic acid from nitriles by contacting a nitrile with a nitrilase according to any one of the above claims. Preferably, the reaction proceeds in the presence of water, that is to say in an aqueous medium. Preferably, the method serves for producing a carboxylic acid selected from the group consisting of 4-cyanopentanoic acid, 2-(1-cyanocyclohexyl)acetic acid, and benzoic acid.

The examples hereinafter serve for more detailed illustration of the invention, but are not to be interpreted as restrictive.

EXAMPLES

The enzyme variants were produced using conventional methods and examined with respect to their properties. For providing the enzyme variants, first the mutations were introduced at the gene level by usual molecular-biological methods. The genes of the enzyme variants were cloned in expression vectors. Then, *Escherichia coli* expression strains were transformed thereby. The DNA plasmid contained the information for regulation of expression of the enzyme variants. The sequence encoding the enzyme or the enzyme variant was placed in this case under the control of an inducible promoter. As a result, by adding an inducer, the expression of the enzyme variants was able to be controlled (generally, isopropyl-β-D-thiogalactopyranoside (IPTG) was used). The *E. coli* strains thus transformed were then cultured in conventional nutrient media (e.g. Lennox broth, minimal medium M9) and induced with IPTG. After expression, the biomass was harvested by centrifugation. The enzyme variants were obtained from the biomass after appropriate cell lysis and purified. In this process, centrifugation, precipitation, ultrafiltration and/or chromatographic methods were used.

The enzyme variants described have the increases in activity shown in Table 3 compared with the parent enzyme using 3 different nitrile substrates.

TABLE 3

| Position | Enzyme (Seq ID No: 2) | 2MG 100% | CH-Dinitrile 100% | Benzonitrile 100% |
|---|---|---|---|---|
| 9 | Leu9Lys | 134% | 131% | 98% |
|  | Leu9Glu | 160% | 177% | 114% |
|  | Leu9Ile | 147% | 171% | 100% |
| 63 | Val63Ile | 163% | 238% | 90% |
|  | Val63Met | 165% | 183% | 97% |
|  | Val63Pro | 142% | 198% | 89% |
|  | Val63Thr | 173% | 175% | 99% |
| 70 | Thr70Ala | 124% | 183% | 111% |
|  | Thr70Cys | 149% | 153% | 128% |
|  | Thr70Asp | 136% | 224% | 114% |
|  | Thr70Glu | 125% | 207% | 113% |
|  | Thr70Phe | 132% | 170% | 104% |
|  | Thr70Gly | 134% | 230% | 114% |
|  | Thr70Ile | 123% | 151% | 113% |
|  | Thr70Leu | 128% | 200% | 105% |
|  | Thr70Met | 122% | 180% | 102% |
|  | Thr70Asn | 122% | 216% | 108% |
|  | Thr70Pro | 126% | 206% | 99% |
|  | Thr70Gln | 129% | 222% | 118% |
|  | Thr70Ser | 138% | 177% | 122% |
|  | Thr70Tyr | 130% | 164% | 103% |
| 94 | Arg94Glu | 111% | 107% | 97% |
|  | Arg94Phe | 117% | 97% | 113% |
|  | Arg94Gly | 123% | 63% | 110% |
|  | Arg94Lys | 112% | 98% | 95% |
|  | Arg94Met | 125% | 80% | 110% |
|  | Arg94Asn | 120% | 81% | 101% |
|  | Arg94Pro | 113% | 97% | 101% |
|  | Arg94Gln | 118% | 101% | 108% |
| 194 | Leu194Cys | 117% | 105% | 71% |
|  | Leu194Lys | 121% | 67% | 73% |
|  | Leu194Met | 116% | 121% | 68% |
|  | Leu194Tyr | 118% | 122% | 76% |
| 208 | Thr208Ala | 144% | 194% | 124% |
|  | Thr208Gly | 154% | 181% | 131% |
|  | Thr208Leu | 132% | 152% | 123% |
| 250 | Cys250Ala | 112% | 221% | 41% |
|  | Cys250Phe | 111% | 194% | 40% |
|  | Cys250Gly | 126% | 281% | 40% |
|  | Cys250Lys | 135% | 97% | 45% |
|  | Cys250Met | 125% | 146% | 40% |
|  | Cys250Arg | 124% | 165% | 39% |
|  | Cys250Ser | 128% | 246% | 40% |
|  | Cys250Thr | 104% | 186% | 38% |
|  | Cys250Tyr | 116% | 196% | 39% |
| 305 | Val305Leu | 126% | 98% | 116% |
|  | Val305Met | 128% | 76% | 116% |
| 308 | Asp308Asn | 133% | 118% | 104% |
|  | Asp308Trp | 128% | 105% | 92% |

Table 4 shows single substitutions according to the invention and residual activities thereof after a 15-minute treatment at 55° C. or 60° C.

TABLE 4

| Position | Enzyme Seq ID No: 2 | 55° C. 57% | Increase in residual activity in % | 60° C. 14% | Increase in residual activity in % |
|---|---|---|---|---|---|
| 9 | Leu9Lys | 80% | 40% | 20% | 43% |
|  | Leu9Glu | 83% | 45% | 35% | 151% |
|  | Leu9Ile | 73% | 28% | 46% | 229% |
|  | Leu9Arg | 89% | 56% | 71% | 409% |
| 63 | Val63Pro | 68% | 19% | 19% | 36% |
|  | Val63Ile | 64% | 12% | 15% | 7% |
| 70 | Thr70Ile | 68% | 19% | 25% | 79% |
|  | Thr70Cys | 59% | 4% | 30% | 118% |
|  | Thr70Phe | 76% | 33% | 4% | −71% |
|  | Thr70Leu | 85% | 50% | 22% | 56% |
|  | Thr70Met | 67% | 18% | 19% | 37% |
|  | Thr70Arg | 82% | 44% | 40% | 188% |
|  | Thr70Val | 91% | 60% | 41% | 190% |
|  | Thr70Tyr | 98% | 72% | 46% | 231% |
| 94 | Arg94Gln | 81% | 42% | 18% | 29% |
|  | Arg94Ala | 90% | 58% | 66% | 370% |
|  | Arg94Glu | 82% | 44% | 38% | 173% |
|  | Arg94Phe | 85% | 49% | 16% | 16% |
|  | Arg94Gly | 89% | 57% | 8% | −40% |
|  | Arg94His | 79% | 39% | 30% | 112% |
|  | Arg94Ile | 96% | 68% | 63% | 354% |
|  | Arg94Lys | 85% | 49% | 49% | 247% |
|  | Arg94Leu | 96% | 69% | 68% | 385% |
|  | Arg94Met | 93% | 63% | 6% | −56% |
|  | Arg94Asn | 91% | 60% | 40% | 189% |
|  | Arg94Pro | 77% | 35% | 36% | 156% |
|  | Arg94Ser | 93% | 64% | 57% | 310% |
|  | Arg94Thr | 88% | 54% | 42% | 198% |
|  | Arg94Val | 77% | 35% | 29% | 111% |
|  | Arg94Tyr | 95% | 66% | 59% | 320% |
| 168 | Phe168Val | 94% | 65% | 62% | 343% |
| 250 | Cys250Gly | 80% | 40% | 20% | 43% |
|  | Cys250Ala | 85% | 49% | 40% | 183% |
|  | Cys250Phe | 90% | 58% | 48% | 240% |
|  | Cys250His | 98% | 73% | 61% | 335% |
|  | Cys250Met | 79% | 38% | 44% | 213% |
|  | Cys250Arg | 77% | 35% | 36% | 158% |
|  | Cys250Ser | 61% | 7% | 21% | 51% |
|  | Cys250Tyr | 99% | 73% | 68% | 384% |
| 305 | Val305Leu | 99% | 74% | 28% | 100% |
|  | Val305Met | 79% | 39% | 45% | 219% |

Table 5 shows the activity of multiple mutants according to the invention in comparison with the parent enzyme (Seq ID No: 2), in which the combination of single substitutions leads to a synergistic improvement in the activity of the enzyme:

TABLE 5

| Enzyme mutant | Substrate 2MG | Benzonitrile |
|---|---|---|
| Seq ID No: 2 | 100% | 100% |
| V63P | 142% | 89% |
| C250G | 126% |  |
| V63P/F168V (Seq ID No: 5) |  | 171% |
| V63P/C250G (Seq ID No: 3) | 206% |  |

The invention claimed is:

1. A nitrilase comprising an amino acid sequence having at least 85% homology with the amino acid sequence of SEQ ID NO: 2, which, in comparison with the nitrilase having the amino acid sequence of SEQ ID NO: 2, (i) has an activity increased by at least 15% in the reaction of a nitrile to the corresponding carboxylic acid, wherein the nitrile is selected from the group consisting of 2-methylglutaronitrile, 1-(cyanomethyl)cyclohexane-1-carbonitrile and benzonitrile;

and/or (ii) has at least one amino acid substitution selected from the group consisting of:

a) substitution of Leu in the position which corresponds to position 9 of SEQ ID NO: 2 by an amino acid selected from the group consisting of Arg, Glu, Ile, and Lys;

b) substitution of Val in the position which corresponds to position 63 of SEQ ID NO: 2 by an amino acid selected from the group consisting of Ile, Met, Pro, and Thr;

c) substitution of Thr in the position which corresponds to position 70 of SEQ ID NO: 2 by an amino acid selected from the group consisting of Ala, Arg, Asn, Asp, Cys, Gln, Glu, Gly, Ile, Leu, Met, Phe, Pro, Ser, Tyr and Val;

d) substitution of Arg in the position which corresponds to position 94 of SEQ ID NO: 2 by an amino acid selected from the group consisting of Ala, Asn, Gln, Glu, Gly, His, Ile, Leu, Lys, Met, Phe, Pro, Ser, Thr, Tyr and Val;

e) substitution of Leu in the position which corresponds to position 194 of SEQ ID NO: 2 by an amino acid selected from the group consisting of Cys, Lys, Met, and Tyr;

f) substitution of Thr in the position which corresponds to position 208 of SEQ ID NO: 2 by an amino acid selected from the group consisting of Ala, Gly, and Leu;
g) substitution of Cys in the position which corresponds to position 250 of SEQ ID NO: 2 by an amino acid selected from the group consisting of Ala, Arg, Gly, His, Lys, Met, Phe, Ser, Thr, and Tyr;
h) substitution of Val in the position which corresponds to position 305 of SEQ ID NO: 2 by an amino acid selected from the group consisting of Leu and Met; and
i) substitution of Asp in the position which corresponds to position 308 of SEQ ID NO: 2 by an amino acid selected from the group consisting of Asn, and Trp.

2. The nitrilase as claimed in claim 1, which has at least two amino acid substitutions selected from the group consisting of a), b), c), d), e), f), g), h) and i).

3. The nitrilase as claimed in claim 1, which has at least three amino acid substitutions selected from the group consisting of a), b), c), d), e), f), g), h) and i).

4. The nitrilase as claimed in claim 1, which additionally has at least one further amino acid substitution selected from the group consisting of:
j) substitution of Tyr in the position which corresponds to position 65 of SEQ ID NO: 2 by an amino acid selected from the group consisting of Ala, Arg, Asn, Asp, Cys, Gln, Glu, Gly, His, Ile, Leu, Lys, Met, Phe, Pro, Ser, Thr, Trp and Val;
k) substitution of Phe in the position which corresponds to position 168 of SEQ ID NO: 2 by an amino acid selected from the group consisting of Ala, Arg, Asn, Asp, Cys, Gln, Glu, Gly, His, Ile, Leu, Lys, Met, Pro, Ser, Thr, Trp, Tyr and Val;
l) substitution of Phe in the position which corresponds to position 174 of SEQ ID NO: 2 by an amino acid selected from the group consisting of Ala, Arg, Asn, Asp, Cys, Gln, Glu, Gly, His, Ile, Leu, Lys, Met, Pro, Ser, Thr, Trp, Tyr and Val;
m) substitution of Ile in the position which corresponds to position 201 of SEQ ID NO: 2 by an amino acid selected from the group consisting of Ala, Arg, Asn, Asp, Cys, Gln, Glu, Gly, His, Leu, Lys, Met, Phe, Pro, Ser, Thr, Trp, Tyr and Val; and
n) substitution of Thr in the position which corresponds to position 210 of SEQ ID NO: 2 by an amino acid selected from the group consisting of Ala, Arg, Asn, Asp, Cys, Gln, Glu, Gly, His, Ile, Leu, Lys, Met, Phe, Pro, Ser, Tip, Tyr and Val.

5. The nitrilase as claimed in claim 1, having a residual activity after a temperature treatment that is at least 10% more than the residual activity of a nitrilase having the sequence of SEQ ID NO: 2 after the temperature treatment, wherein the residual activity is with respect to the reaction of a nitrile to the corresponding carboxylic acid, wherein the nitrile is selected from the group consisting of 2-methylglutaronitrile, 1-(cyanomethyl)cyclohexane-1-carbonitrile and benzonitrile and wherein the temperature treatment is incubating the nitrilase in 100 mm potassium phosphate buffer pH 7.0 with 1 mm DTT for 15 min at 55° C.

6. A nitrilase comprising an amino acid sequence having at least 98% homology with the amino acid sequence of SEQ ID NO: 8.

7. A method for producing a carboxylic acid from nitriles by contacting a nitrile with a nitrilase as claimed in claim 1.

8. The method as claimed in claim 7 for producing a carboxylic acid selected from the group consisting of 4-cyanopentanoic acid, 3-hydroxyvaleric acid and glycolic acid.

9. A nitrilase of claim 1 comprising the amino acid sequence of SEQ ID NO: 2 having one or more amino acid substitution and having an activity that is increased by at least 15% in the reaction of a nitrile to the corresponding carboxylic acid, wherein the nitrile is selected from the group consisting of 2-methylglutaronitrile, 1-(cyanomethyl)cyclohexane-1-carbonitrile and benzonitrile, wherein the at least one amino acid substitutions is selected from the group consisting of:
a) substitution of Leu in the position which corresponds to position 9 of SEQ ID NO: 2 by Lys, Glu, Ile or Arg;
b) substitution of Val in the position which corresponds to position 63 of SEQ ID NO: 2 by Pro, Ile, Met or Thr;
c) substitution of Thr in the position which corresponds to position 70 of SEQ ID NO: 2 by Ile, Ala, Cys, Asp, Glu, Phe, Gly, Leu, Met, Asn, Pro, Gln, Ser, Tyr; Arg or Val;
d) substitution of Arg in the position which corresponds to position 94 of SEQ ID NO: 2 by Gln, Glu, Phe, Gly, Lys, Met, Asn, Pro, Ala, Gly, His, Ile, Leu, Ser, Thr, Val or Tyr;
e) substitution of Leu in the position which corresponds to position 194 of SEQ ID NO: 2 by Tyr, Cys, Lys or Met;
f) substitution of Thr in the position which corresponds to position 208 of SEQ ID NO: 2 by Ala, Gly or Leu;
g) substitution of Cys in the position which corresponds to position 250 of SEQ ID NO: 2 by Gly, Ala, Phe, Lys, Met, Arg, Ser, Thr, Tyr or His;
h) substitution of Val in the position which corresponds to position 305 of SEQ ID NO: 2 by Leu or Met; and
i) substitution of Asp in the position which corresponds to position 308 of SEQ ID NO: 2 by Asn or Trp.

10. A nitrilase of claim 4 comprising the amino acid sequence of SEQ ID NO: 2 wherein at least one of the amino acid substitutions is selected from the group consisting of:
a) substitution of Leu in the position which corresponds to position 9 of SEQ ID NO: 2 by Lys, Glu, Ile or Arg;
b) substitution of Val in the position which corresponds to position 63 of SEQ ID NO: 2 by Pro, Ile, Met or Thr;
c) substitution of Thr in the position which corresponds to position 70 of SEQ ID NO: 2 by Ile, Ala, Cys, Asp, Glu, Phe, Gly, Leu, Met, Asn, Pro, Gln, Ser, Tyr; Arg or Val;
d) substitution of Arg in the position which corresponds to position 94 of SEQ ID NO: 2 by Gln, Glu, Phe, Gly, Lys, Met, Asn, Pro, Ala, Gly, His, Ile, Leu, Ser, Thr, Valor Tyr;
e) substitution of Leu in the position which corresponds to position 194 of SEQ ID NO: 2 by Tyr, Cys, Lys or Met;
f) substitution of Thr in the position which corresponds to position 208 of SEQ ID NO: 2 by Ala, Gly or Leu;
g) substitution of Cys in the position which corresponds to position 250 of SEQ ID NO: 2 by Gly, Ala, Phe, Lys, Met, Arg, Ser, Thr, Tyr or His;
h) substitution of Val in the position which corresponds to position 305 of SEQ ID NO: 2 by Leu or Met;
i) substitution of Asp in the position which corresponds to position 308 of SEQ ID NO: 2 by Asn or Trp
and wherein at least one amino acid substitution is selected from the group consisting of
j) substitution of Tyr in the position which corresponds to position 65 of SEQ ID NO: 2 by an amino acid selected from the group consisting of Ala, Arg, Asn, Asp, Cys, Gln, Glu, Gly, His, Ile, Leu, Lys, Met, Phe, Pro, Ser, Thr, Trp and Val;
k) substitution of Phe in the position which corresponds to position 168 of SEQ ID NO: 2 by an amino acid selected from the group consisting of Ala, Arg, Asn, Asp, Cys, Gln, Glu, Gly, His, Ile, Leu, Lys, Met, Pro, Ser, Thr, Trp, Tyr and Val;

j) substitution of Phe in the position which corresponds to position 174 of SEQ ID NO: 2 by an amino acid selected from the group consisting of Ala, Arg, Asn, Asp, Cys, Gln, Glu, Gly, His, Ile, Leu, Lys, Met, Pro, Ser, Thr, Trp, Tyr and Val;

m) substitution of Ile in the position which corresponds to position 201 of SEQ ID NO: 2 by an amino acid selected from the group consisting of Ala, Arg, Asn, Asp, Cys, Gln, Glu, Gly, His, Leu, Lys, Met, Phe, Pro, Ser, Thr, Trp, Tyr and Val; and n) substitution of Thr in the position which corresponds to position 210 of SEQ ID NO: 2 by an amino acid selected from the group consisting of Ala, Arg, Asn, Asp, Cys, Gln, Glu, Gly, His, Ile, Leu, Lys, Met, Phe, Pro, Ser, Trp, Tyr and Val.

11. The nitrilase as claimed in claim 9, which has at least two amino acid substitutions selected from the group consisting of a), b), c), d), e), f), g), h) and i).

12. The nitrilase as claimed in claim 9, which has at least three amino acid substitutions selected from the group consisting of a), b), c), d), e), f), g), h) and i).

13. The nitrilase as claimed in claim 9, having a residual activity after a temperature treatment that is increased by at least 10% with respect to the reaction of a nitrile to the corresponding carboxylic acid, wherein the nitrile is selected from the group consisting of 2-methylglutaronitrile, 1-(cyanomethyl)cyclohexane-carbonitrile and benzonitrile wherein the temperature treatment is incubating the nitrilase in 100 mM potassium phosphate buffer pH 7.0 with 1 mM DTT for 15 min at 55° C. or 60° C.

14. A method for producing a carboxylic acid from nitriles by contacting a nitrile with a nitrilase as claimed in claim 9.

15. The method as claimed in claim 14 for producing a carboxylic acid selected from the group consisting of 4-cyanopentanoic acid, 3-hydroxyvaleric acid and glycolic acid.

16. A nitrilase comprising an amino acid sequence having at least 85% homology with the amino acid sequence of SEQ ID NO: 2, which, in comparison with the nitrilase having the amino acid sequence of SEQ ID NO: 2, (i) has an activity increased by at least 15% in the reaction of a nitrile to the corresponding carboxylic acid, wherein the nitrile is selected from the group consisting of 2-methyl glutaronitrile, 1-(cyanomethyl)cyclohex ane-1-carbonitrile and benzonitrile; and (ii) has at least one amino acid substitution selected from the group consisting of:

a) substitution of Leu in the position which corresponds to position 9 of SEQ ID NO: 2 by an amino acid selected from the group consisting of Arg, Glu, Ile, and Lys;

b) substitution of Val in the position which corresponds to position 63 of SEQ ID NO: 2 by an amino acid selected from the group consisting of Ile, Met, Pro, and Thr;

c) substitution of Thr in the position which corresponds to position 70 of SEQ ID NO: 2 by an amino acid selected from the group consisting of Ala, Arg, Asn, Asp, Cys, Gln, Glu, Gly, Ile, Leu, Met, Phe, Pro, Ser, Tyr and Val;

d) substitution of Arg in the position which corresponds to position 94 of SEQ ID NO: 2 by an amino acid selected from the group consisting of Ala, Asn, Gln, Glu, Gly, His, Ile, Leu, Lys, Met, Phe, Pro, Ser, Thr, Tyr and Val;

e) substitution of Leu in the position which corresponds to position 194 of SEQ ID NO: 2 by an amino acid selected from the group consisting of Cys, Lys, Met, and Tyr;

f) substitution of Thr in the position which corresponds to position 208 of SEQ ID NO: 2 by an amino acid selected from the group consisting of Ala, Gly, and Leu;

g) substitution of Cys in the position which corresponds to position 250 of SEQ ID NO: 2 by an amino acid selected from the group consisting of Ala, Arg, Gly, His, Lys, Met, Phe, Ser, Thr, and Tyr;

h) substitution of Val in the position which corresponds to position 305 of SEQ ID NO: 2 by an amino acid selected from the group consisting of Leu, and Met; and i) substitution of Asp in the position which corresponds to position 308 of SEQ ID NO: 2 by an amino acid selected from the group consisting of Asn and Tip.

* * * * *